United States Patent [19]
Champion et al.

[11] Patent Number: 5,868,709
[45] Date of Patent: Feb. 9, 1999

[54] PORTABLE MODULAR APPARATUS AND METHOD FOR DESTROYING MEDICAL NEEDLES

[75] Inventors: Edward R Champion, Kennesaw; John S Lou, Sandy Springs, both of Ga.

[73] Assignee: Medfuse International, Inc., Kennesaw, Ga.

[21] Appl. No.: 864,481

[22] Filed: May 28, 1997

Related U.S. Application Data

[60] Provisional application No. 60/018,456 May 28, 1996.
[51] Int. Cl.[6] ............................................. A61M 5/00
[52] U.S. Cl. ............................ 604/110; 219/68; 219/69.1
[58] Field of Search .................................. 604/110, 187; 219/68, 69.1

[56] References Cited

U.S. PATENT DOCUMENTS

| | | | |
|---|---|---|---|
| 4,628,169 | 12/1986 | Ch'ing-Lung | 219/68 |
| 4,877,934 | 10/1989 | Spinello | 219/68 |
| 4,965,426 | 10/1990 | Colombo | 219/68 |
| 5,076,178 | 12/1991 | Kohl et al. | 110/250 |
| 5,091,621 | 2/1992 | Butler | 219/68 |
| 5,138,124 | 8/1992 | Kirk et al. | 219/68 |
| 5,138,125 | 8/1992 | Salesses | 219/68 |
| 5,212,362 | 5/1993 | Burden et al. | 219/69.1 |
| 5,245,935 | 9/1993 | Fukuda | 110/250 |
| 5,264,675 | 11/1993 | Butler | 219/68 |
| 5,268,549 | 12/1993 | Butler | 219/68 |
| 5,282,428 | 2/1994 | Greville et al. | 110/250 |
| 5,288,964 | 2/1994 | Walker et al. | 219/68 |
| 5,294,767 | 3/1994 | Cantarero | 219/68 |
| 5,300,752 | 4/1994 | Elmerick et al. | 219/68 |
| 5,329,087 | 7/1994 | Kohl et al. | 219/68 |
| 5,334,812 | 8/1994 | Ch-ing Lung | 219/68 |
| 5,336,862 | 8/1994 | Yelvington | 219/68 |
| 5,365,029 | 11/1994 | Makihara | 219/68 |
| 5,468,928 | 11/1995 | Yelvington | 219/68 |
| 5,525,772 | 6/1996 | Tanguy | 219/68 |
| 5,540,416 | 7/1996 | Huang | 266/200 |
| 5,545,869 | 8/1996 | Piva | 219/68 |
| 5,548,095 | 8/1996 | Cornell | 219/68 |
| 5,551,355 | 9/1996 | Haines et al. | 110/242 |

*Primary Examiner*—John D. Yasko

[57] ABSTRACT

A portable electronic (electro-mechanical) device for destroying sharp, contaminated hypodermic and other medical needles includes an upper electrode assembly, two fixed, and one moveable electrode situated between the two fixed electrodes. The moveable electrode comprises a chamber to contain residue and sparks generated from closing an electrical circuit. An electronic control circuit controls the modulation of the moveable electrode in relation to the two fixed electrodes and automatically manages the destruction cycle of said needle by use of electro-mechanical sensors and motors. The sharp end of said needle is inserted through an opening in the upper electrode and contacts the lower fixed electrode. Any gases generated by the incineration process are drawn through the disposable burn head by a fan and are filtered by a multi-stage filteration system before being passed into the local ambient surroundings. The portable apparatus is modular. The burn head assembly including the electrodes, debris container, fan, multi-stage filter, motors, and the plastic housing is disposable.

4 Claims, 8 Drawing Sheets

PORTABLE MODULAR APPARATUS AND METHOD FOR DESTROYING MEDICAL NEEDLES

CROSS REFERENCES TO RELATED APPLICATIONS

This patent is based upon an application which is relative to provisional patent application number 60/018456 filed May 28, 1996.

BACKGROUND—FIELD OF INVENTION

This invention relates to the medical field, specifically to the method and apparatus for destroying medical hypodermic and related syringe needles, causing immediate destruction of said needle, any pathogens exposed to needle, sealing, blunting, and sterilizing the remaining portion of the needle at the needle hub to prevent the possibility of post-use needle injury. This invention further relates to computer-controlled apparatus using an electro-mechanical modulation method with high electric current to destroy medical needles while removing any gases generated from the incineration process via a fan and multi-stage purification filter system.

BACKGROUND—DESCRIPTION OF PRIOR ART

The primary threat of the post-use, medical syringe needle is the sharp, hollow, metalic portion, and the fluid contained therein. Users of medical needles, consisting of hospital workers, nurses, paramedics, those self-administrating prescribed drugs, and other authorized individuals, need a safe process for disposing medical needles to eliminate the chance of accidental puncture by said needle. The Centers for Disease Control in Atlanta, Ga. have studied the accidental needle injurying incidents and have concluded that medical personnel, nurses in particular, experience a majority of post-use needle injurys in the process of covering, un-covering, transporting, and ultimately disposing of said needle. Attempting to cover the post-use needle is dangerous and may result in accidental stick if not performed correctly. Accidents also occur while un-covering said needles. The result of inadvertent puncture of post-use needles is life threatening.

The transmission of infectious disease, causing grave illness or even death, results from inappropriate handling of said post-use needles. These needles require disposal by means of placing them into an authorized, puncture-proof, disposable container, such as a "sharps container." This container is designed to hold many medical needles and is engineered to ensure these needles will not cause accidental puncturing of an individual handling the container. However, danger still exists for an individual, while handling said container, to be accidentally punctured by post-use needles within the container upon disposal of its contents. Attempting to dispose of medical needles is a serious task which requires a great deal of caution to guarantee an individual does not accidentally stick themself or another person in the process of attempting the disposal of said needle. In addition, accidental needle stick can occur if an individual attempts to remove said needles from the container. Therefore, it is advantageous to possess apparatus to completely destroy said needle at the point of use which will alleviate the transportation of said used needle, and the possibility of inadvertent stick of post-use needle. The effective destruction of said needles will reduce the chance of spreading disease at point of use. The remaining portion of the medical syringe can be properly disposed with significantly reduced risk of injury.

All of the reference U.S. and foreign patents listed in the cover sheet of this document, including this invention, use electrical current to destroy syringe needles. Most earlier forms of destroying syringe needles use an electrical current passing through a portion of a needle which comes in contact with two electrodes of varying electrical potential.

An earlier method of destroying a syringe needle is depicted in U.S. Pat. No. 4,628,169 to Ch'ing-Lung (Dec. 09, 1986) in which two fixed electrodes are spaced beneath an opening in a housing. A needle is placed through the opening in the housing and contacts both electrodes causing a short-circuit, thereby destroying the section of needle by resistance heating. Continuous insertion of the needle between the electrodes eventually destroys successive portions of the needle. The electrical circuit consists of an alternating current (AC) line cord, transformer, fuse, power switch. There are several drawbacks of this design. First, the distance between the two contacts is finite and does not allow the complete destruction of the syringe needle, leaving a possibly dangerous stub which can potentially puncture anyone coming in contact with the remaining portion of the needle syringe. Second, the alignment of the syringe needle, with respect to the opening in the housing over the contacts, must be maintained to initiate repeatable results. The location of which the device can be used is limited to the AC power source, and fuses must be kept on-hand in case of failure. This electrical current process and approach is covered in U.S. Pat. 4,877,934 to Spinello (Oct. 31, 1989) and U.S. Pat. No. 4,965,426 to Colombo (Oct. 23, 1990). However, these devices do leave the remaining un-burned portion of the needle barrel not sealed or sometimes partially sealed. This lack of sealing allows contaminates to flow into the ambient surrounding. U.S. Pat. No. 5,076,178 to Kohl et. al. (Dec. 31, 1991) allows for crimping of the needle barrel prior to passing an electrical through the needle barrel.

This device does not provide an 100% effective method of sealing the un-burned needle barrel and the crimping may fracture the needle barrel before an electrical current is applied thereby leaving an uncontrolled burn process which could afford the possibility to allow pathogens to escape during the destruction of the needle. This process could be in violation of Federal Regulation Volume 56, No. 235, Sect. 1910–1030 that prohibits the shearing or breaking of contaminated needles. This device requires 110 to 120 VAC continuous and is not portable.

Further development in the methods and apparatus for the needle destruction process are indicated in U.S. Pat. No. 5,551,355 to Haines, et. al. (Sep. 03, 1996), U.S. Pat. No. 5,525,772 to Tanguy (Jun. 11, 1996), U.S. Pat. No. 5,540, 416 to Huang (Jul. 30, 1996), and U.S. Pat. No. 5,468,928 to Yelvington (Nov. 01, 1995). In general, not much attention is given to disposal methods of the waste (needle debris) and the method to modulate the current into the needle to insure a consistent burn and a 100% probability of syringe sealing after the needle barrel is burned and severed from the syringe. In addition gases, that may contain airborne pathogens produced by the needle destruction process, are allowed to escape to surrounding areas. Therefore, it is seen that there exists a need for an apparatus for safely and effectively sterilizing and destroying the metal needle component of medical needles.

What is needed is a portable, easy to use device to effectively destroy post-use medical needles and render the remaining portion of said needle harmless. In addition, a requirement is minimized operator intervention and minimized mechanical parts and is compilant with Federal Regulations. The present invention minimizes pathogen exposure by making disposable the entire burn head unit. This device should also use a method of effectively destroying said needle while containing byproducts generated during the destruction of said needle.

OBJECTS AND ADVANTAGES

Accordingly, several objects and advantages of the current invention are:

It is, therefore, an object of the invention to provide a portable, easily disposable apparatus that can be situated at the point of use for destroying medical needles by using electrical resistance heating to reduce or eliminate post-use handling injury.

It is another object of the invention to provide a method of destroying medical needles by an electromechanical modulation of electrodes.

It is another object of the invention to control operation of invention by computer.

It is another object of the invention to provide modular housing of electrical and mechanical components for disposal of waste generated by destroying medical needles.

It is still another object of the invention to contain the waste generated by the destruction of medical needles by a sealed, integral waste container.

It is another object of the invention to provide a rechargeable power source to supply sufficient energy to power electro-mechanical components of apparatus and destroy medical needles.

It is still another object of the invention to provide integral means to recharge power source.

It is yet still another object of the invention to provide indicators to communicate status of unit operation.

It is further an object of the invention to provide means of venting and filtering gases, thereby minimizing possible emissions of bio-hazardous, airborne pathogens that may produced while destroying medical needles.

Still further objects and advantages will become apparent from a consideration of the ensuing description and accompanying drawings.

Figure 1:
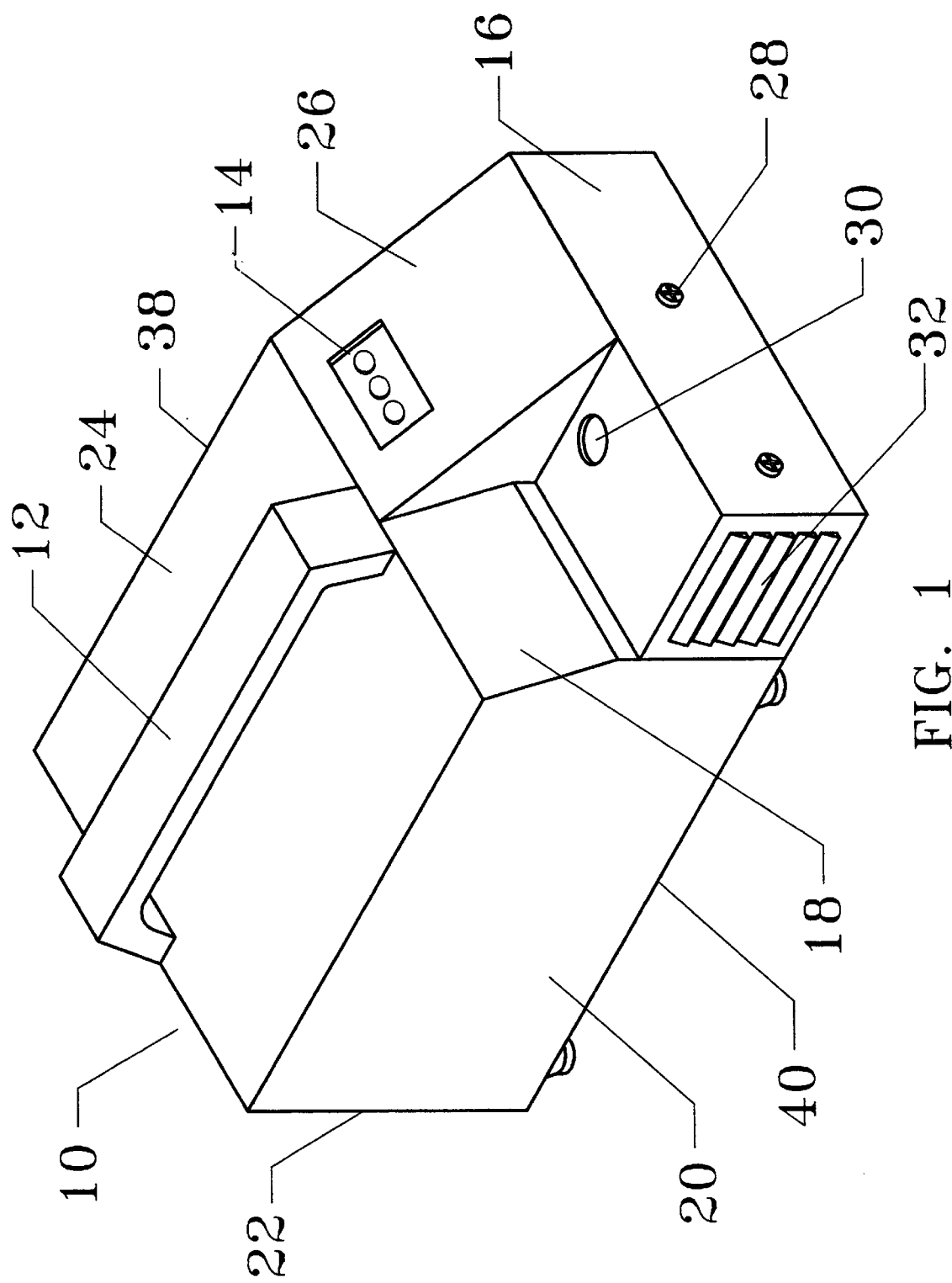
FIG. 1 is a perspective view of the present invention

REFERENCE NUMERALS 10 present invention
12 handle
14 status indicators
16 burn module
18 front surfaces
20 side surfaces
22 end surface
24 top surface
26 slope surface
28 burn module fastener
30 medical needle aperture
32 air inlet opening
34 power connector
36 power switch
38 main module housing cover
40 main module base
42 status indicator board
44 elevated support
46 main module fastener
48 module retaining wall
50 module fastener sleeve
52 module retainer
54 rechargable battery
56 burn module protector
58 controller board
60 input protector
62 module power switch
64 battery charger
66 computer
68 status indicator interface
70 terminal connectors
72 controller board guides
74 status indicator wiring harness
76 burn module signal connector
78 burn module power connectors
80 air exit opening
82 burn module base
84 burn module cover
86 fan
88 multi-stage filter
90 burn unit assembly
92 elevated supports
94 fasteners
96 medical needle sensor
98 medical needle
100 medical needle hub
102 burn module identification unit
104 burn unit assembly housing
106 upper electrode assembly
108 contact retainer
110 retainer spring
112 upper electrode contactor
114 upper insulator
116 moveable electrode
118 lower insulator
120 lower electrode
122 burn head mounting plate
124 left motor drive assembly
126 right motor drive assembly
128 burn head assembly retainers
130 burn head electrode connectors
132 movable electrode retainers
134 upper electrode aperture
136 moveable electrode lower wiper
138 moveable electrode upper wiper
140 moveable electrode waste cover
142 waste cavity

SUMMARY

The present invention is a device for destroying biologically hazardous medical needles having an electrically conductive, hollow shaft with one sharp end and rendering the remaining syringe/needle nub blunt and sealed such that no potential for post-use injury either by stick or accidental scratch or infection transmission can occur. The present invention uses computer controlled electronic resistance heating to destroy the majority of a medical needle consistantly while sealing any contaminant from the local ambient environment and reducing post-use injury or infection transmission.

PREFERRED EMBODIMENT—DESCRIPTION

With reference to figures, the present invention 10 comprises a main module housing cover 38, handle 12, status indicators 14, main module base 40, and burn module 16. The present invention 10 is generally rectangular in shape and defined with front surfaces 18, side surfaces 20, end surface 22, top surface 24, and slope surface 26 which accommodates a plurality of status indicators 14. The main module base 40 and burn module 16 are generally attached and can be removed at front surface 18 by means of burn module fastener 28. The burn module 16 is generally rectangular in shape and comprises a medical needle aperture 30 and air inlet opening 32. The main module housing cover 38, main module base 40, and burn module 16 are generally made of any suitable material, such as metal, plastic or the like, and any combination thereof.

Figure 2:
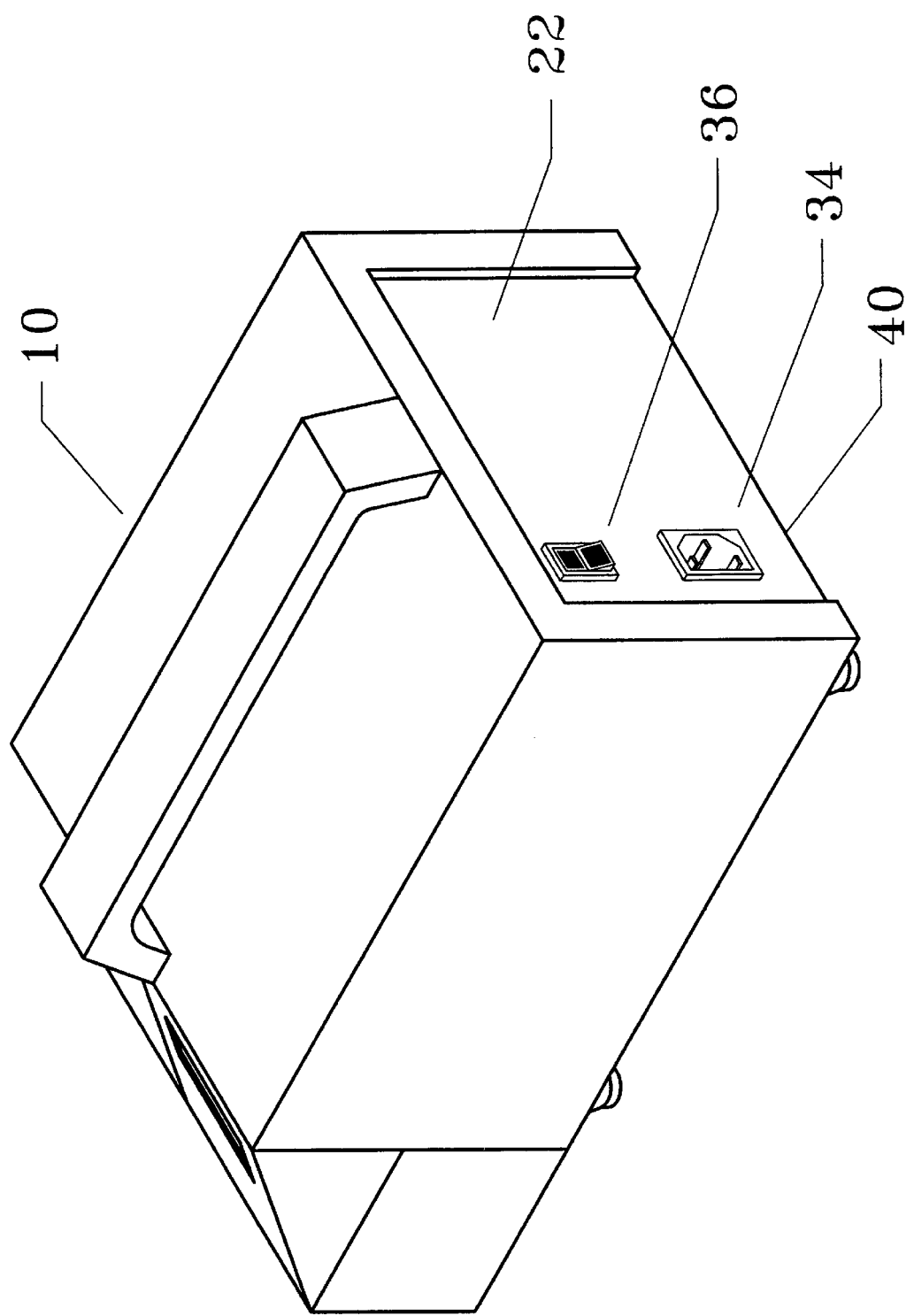
FIG. 2 is a perspective rear view in partial of the device in FIG. 1

FIG. 2 generally denotes the rear of the present invention 10 which comprises power connector 34 and power switch 36 mounted to end surface 22 of main module base 40. The power connector 34 provides general means for connection to external power source for powering the present invention 10.

Figure 3:
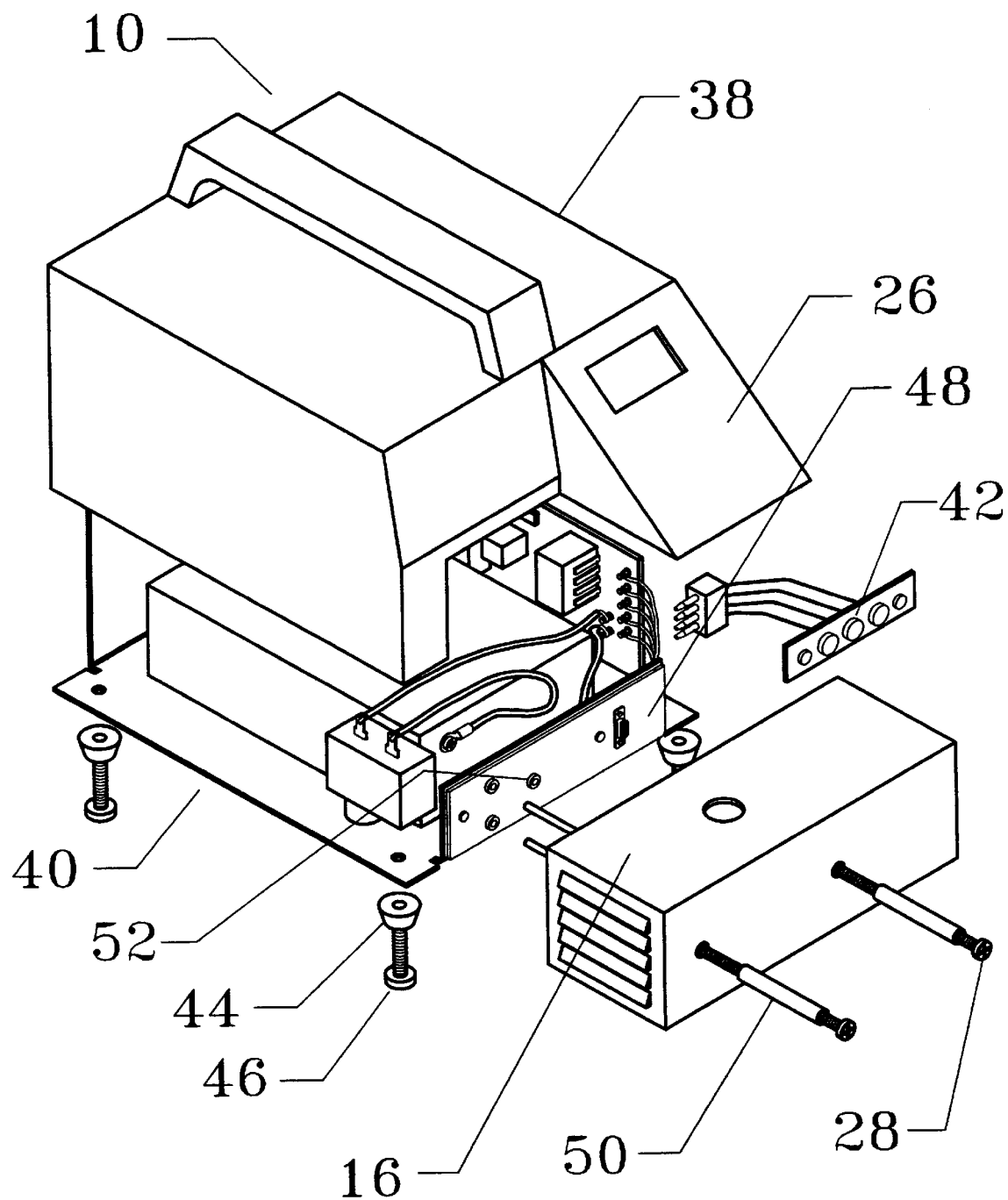
FIG. 3 is an exploded view of the current invention in FIG. 1

Referring to drawings, FIG. 3 generally denotes assembly of of present invention 10 comprising of main module housing cover 38, main module base 40, status indicator board 42, and burn module 16. Status indicator board 42 is secured to interior wall of slope surface 26 on main module housing cover 38. The main module housing cover 38 mounts to main module base 40 and is secured by plurality of elevated support 44 and main module fastener 46 on underside periphery of main module base 40. Burn module 16 mounts flush to module retaining wall 48 at module retainer 52 by means of burn module fastener 28 and module fastener sleeve 50.

Figure 4:
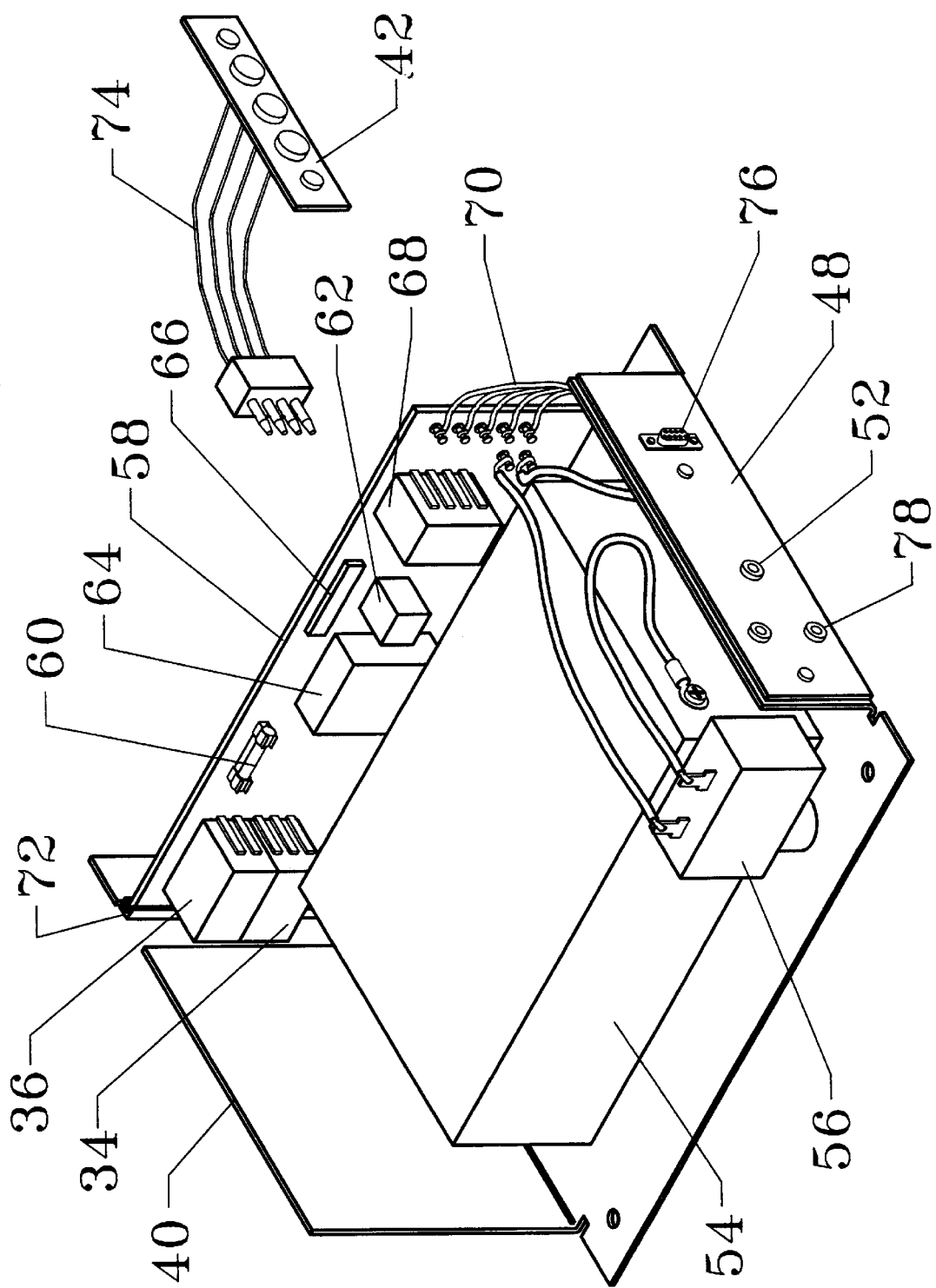
FIG. 4 is an exploded view of a portion of the device in FIG. 3
Figure 5:
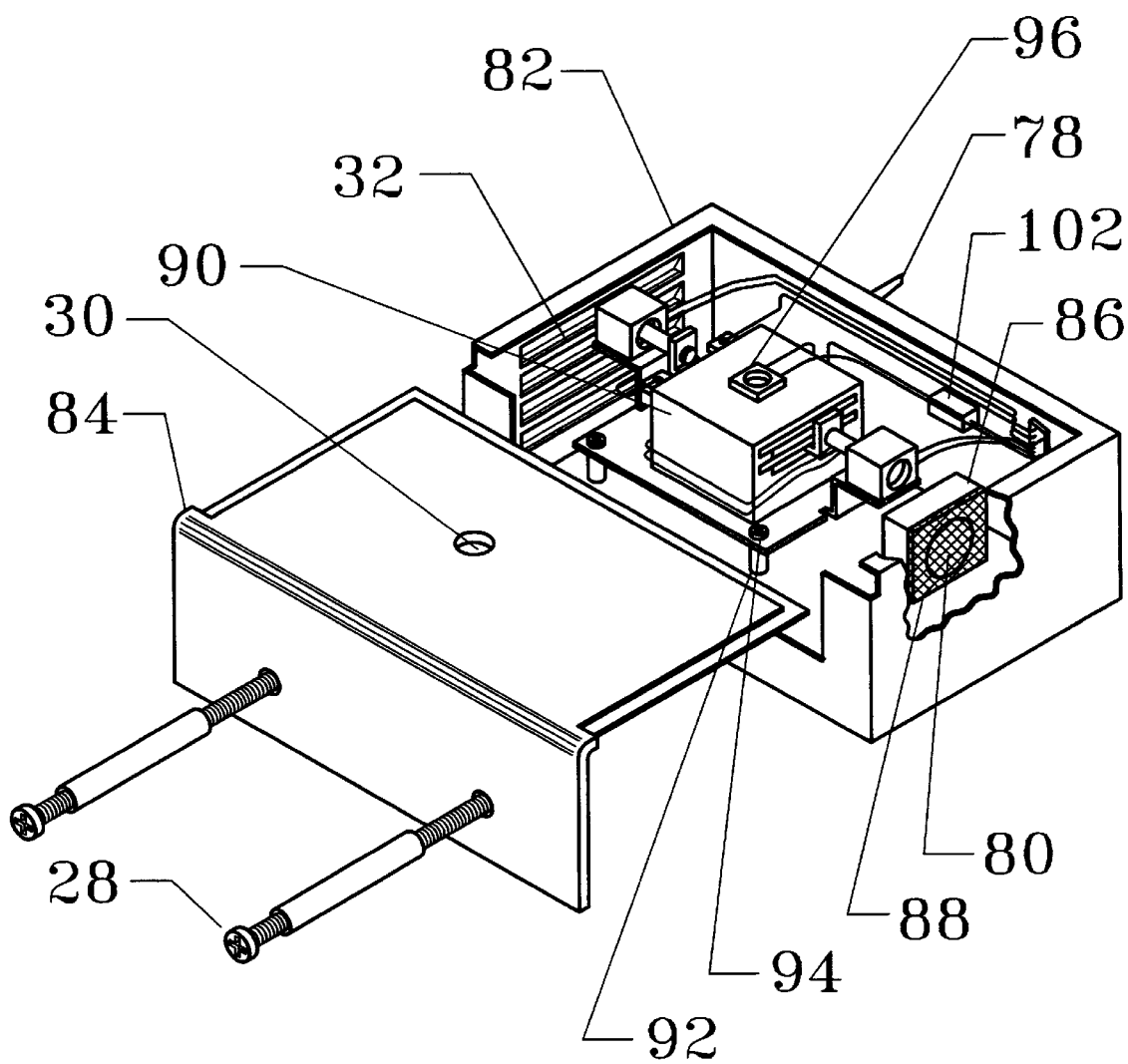
FIG. 5 is a view of a portion of FIG. 3

Referring to drawings, FIG. 4 generally denotes the main module base 40 comprising of rechargable battery 54, burn module protector 56, controller board 58. The controller board 58 generally comprises power connector 34, power switch 36, input protector 60, module power switch 62, battery charger 64, computer 66, status indicator interface 68, and a plurality of terminal connectors 70. The controller board 58 is vertically situated and secured by controller board guides 72. The status indicator board 42 generally connects to controller board 58 at status indicator interface 68 through status indicator wiring harness 74. The module retaining wall 48 comprises burn module signal connector 76, module retainer 52, and burn module power connectors 78.

Referring to FIGS. 1 through 5, the burn module comprises a burn module base 82 and burn module cover 84. The burn module base comprises an air inlet opening 32, and air exit opening 80. A fan 86 and multi-stage filter 88 are directly situated over air exit opening 80, internal to burn module base 82. The module retaining wall 48 comprises a burn module identification unit 102, burn module power connectors 78, and burn module signal connector 76. A burn unit assembly 90 is generally rectangular in shape and is secured to burn module base 82 by elevated supports 92 and fasteners 94 and comprises an opening for entry of medical needle 98. A medical needle sensor 96 is secured to top of burn unit assembly 90 by any suitable means of fastening, and comprises an opening which extends throughout its length. The burn module base 82 and burn module cover 84 are generally composed of the same material, with burn module cover 84 generally L-shaped and mounted to burn module base 82 by means of bonding mating surfaces to have an air-tight seal around the periphery of burn module 16. It is generally expected that air is allowed to enter air inlet opening 32 and medical needle aperture 30, and is exhausted through air exit opening 80. When the burn module cover 84 and burn module base 82 are secured, the medical needle aperture 30 coincides with opening of the medical needle sensor 96 to allow entry of medical needle 98 to travel through medical needle aperture 30, medical needle sensor 96, and enter burn unit assembly 90.

Figure 6:
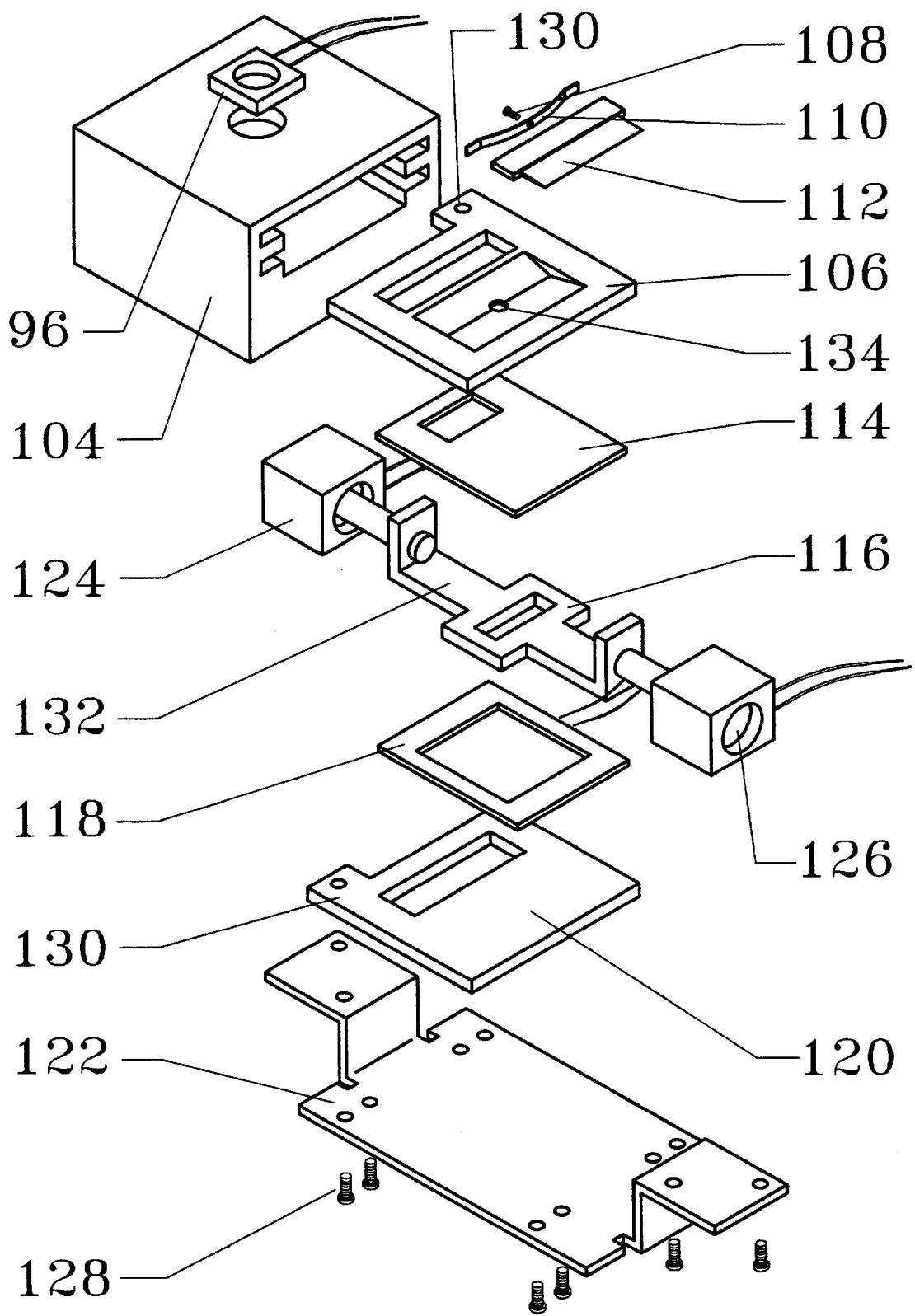
FIG. 6 is an exploded view of a portion of FIG. 5
Figure 7:
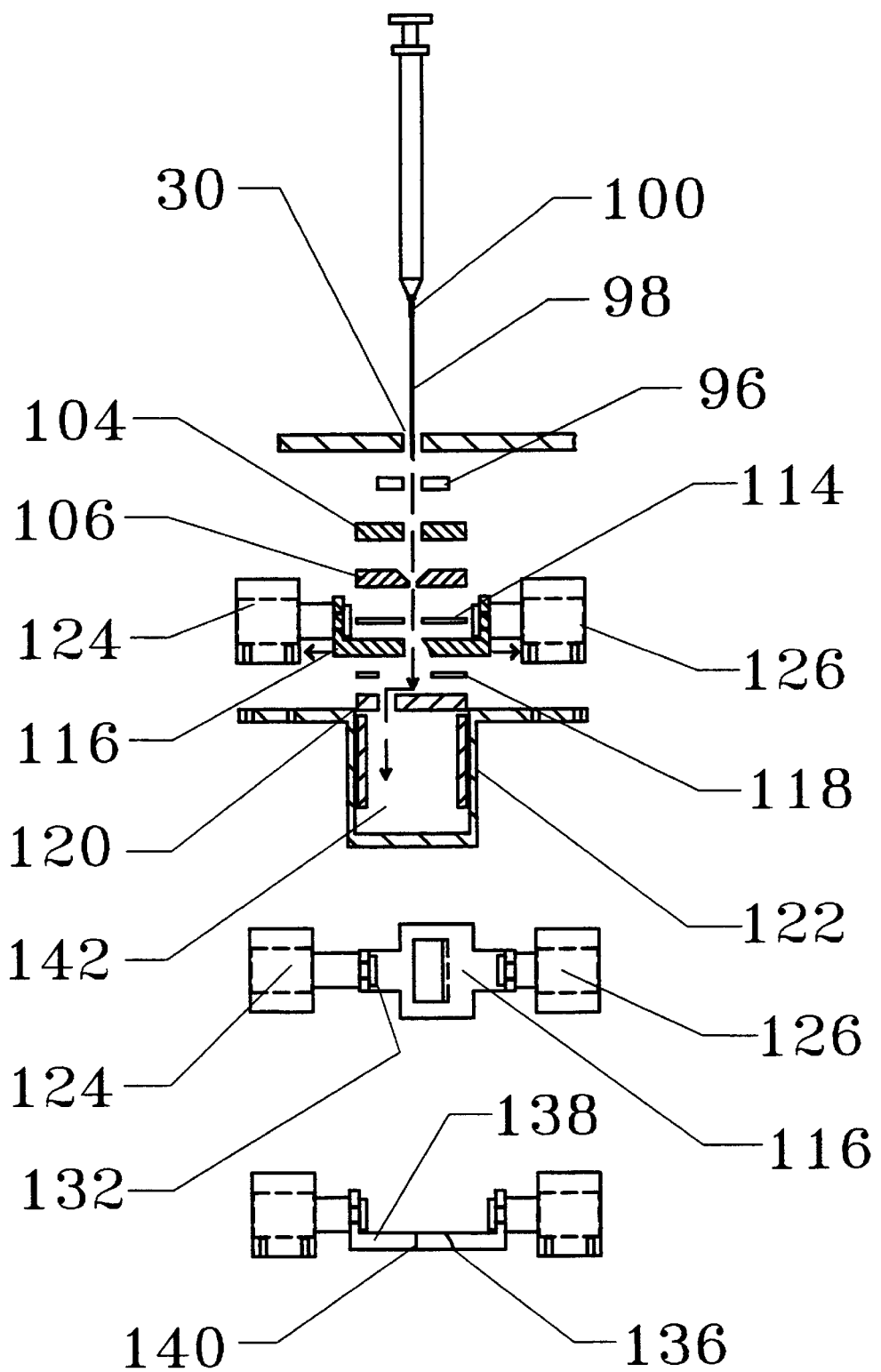
FIG. 7 is a mechanical schematic diagram of FIG. 6.
Figure 8:
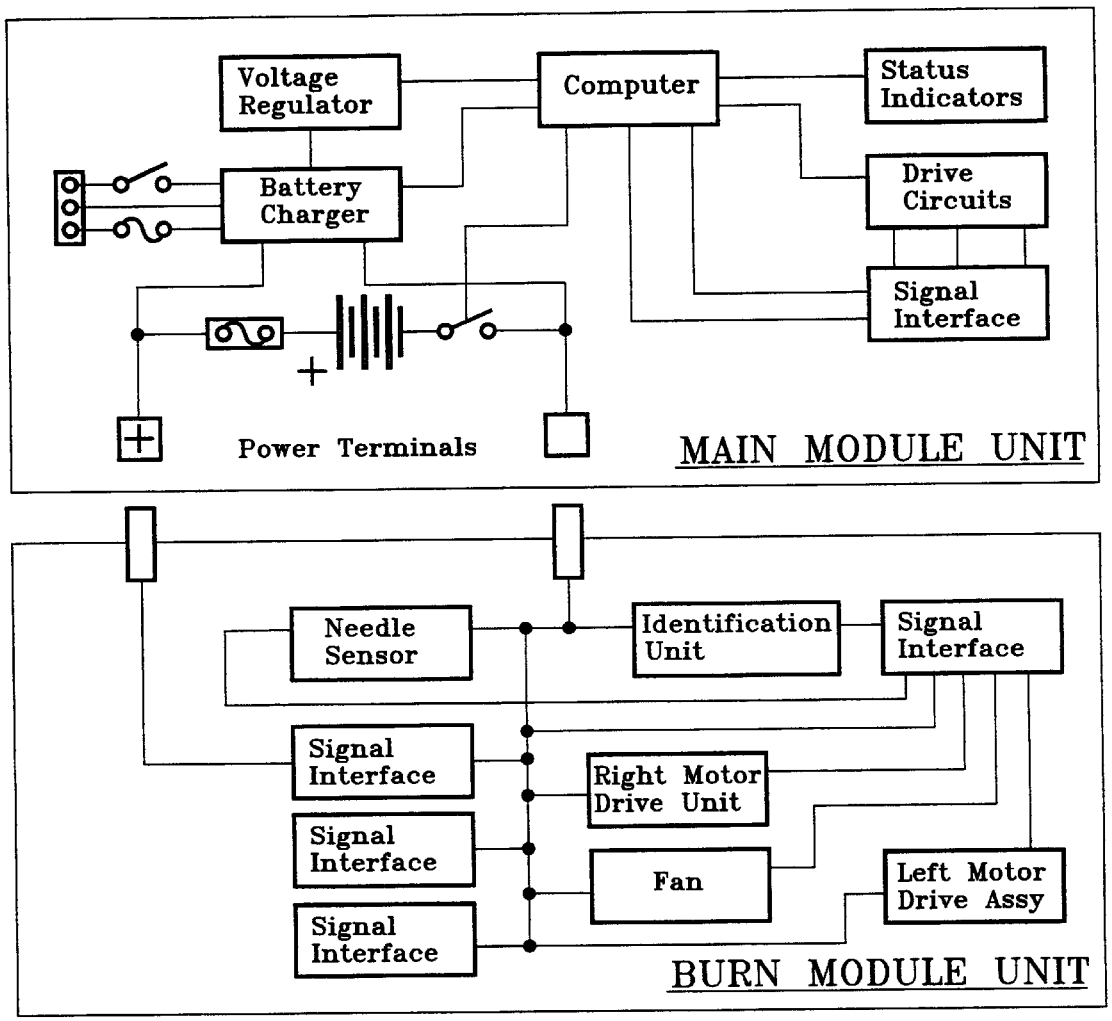
FIG. 8 is an electrical schematic diagram of present invention

Referring to FIGS. 6 through 7, the needle destroying means comprises electrodes arranged in an overlapping manner comprising an upper electrode assembly 106 and moveable electrode 116, and lower electrode 120. The moveable electrode 116 is separated by an upper insulator 114 and lower insulator 118. The burn unit assembly housing 104 respectively aligns said electrodes and insulators and is generally made of suitable material with insulating properties. The upper electrode assembly 106 comprises an upper electrode contactor 112 seated in an upper electrode assembly 106, secured by a contact retainer 108, and slides within said electrode assembly with an applied force directed by a compression retainer spring 110. An upper electrode aperture 134 is situated between upper electrode assembly 106 and upper electrode contactor 112 to accept medical needle 98 through upper electrode assembly 106 with constant force against said sides of needle by upper electrode contactor 112. The moveable electrode 116 is situated between upper insulator 114 and lower insulator 118 with left portion of electrode secured to left motor drive assembly 124 and right portion of moveable electrode 116 secured to right motor drive assembly 126 by movable electrode retainers 132 and slides between insulators in the direction of either motor drive assembly. The left motor drive assembly 124, right motor drive assembly 126, and burn unit assembly housing 104 are mounted to surface of burn head mounting plate 122 with burn head assembly retainers 128. An enclosed waste cavity 142 exists between the space of the lower electrode 120 and burn head mounting plate 122, to accommodate the collection of byproducts from the needle destruction process.

PREFERRED EMBODIMENT—OPERATION

With reference to FIG. 1, the present invention 10 destroys a medical needle 98 by inserting said needle into the medical needle aperture 30. The present invention 10 comprises a computer to control the modulation method used to destroy said needle, outputs status of the apparatus, and enables the destruction of the said needle when the battery is fully charged. The energy needed to melt the needle using electrical current is proportional to the square of the electrical current multiplied by the resistance of the electrical path. This energy factor varies depending on the composition of the needle and the electrical resistance per unit length. The resistance per unit length of an object that conducts current is inversely proportional to the area of the conductor. The medical needle 98 has a hollow interior as opposed to a solid object of similar composition, and therefore has a higher resistance than a solid object of identical composition and exterior dimensions. The type of wire used to connect the current source to the electrodes usually is many times larger than the diameter of the needle and is solid or composed of multiple solid strands of wire that are wound together. The resistance of the medical needle 98 is relatively higher than the current source and electrical wiring used to pass the current though the medical needle 98. Given sufficient current in the circuit with a current source, electrical wiring, contacts, and the medical needle 98, the medical needle 98 will be destroyed in the form of melting in segments. The resistance of the needle, when placed across the opposite charged electrodes, causes the needle to be heated to between 1500° C. and 1800° C. This level of temperature eliminates the active state of any virus, bacteria, yeast, or other microorganism and thereby destroying any pathogen. In addition the operation of the present invention cuts and blunts the medical needle and seals the medical needle tip so that no fluid can leak into the ambient environment.

Referring to FIGS. 1 though 8, the present invention 10 comprises the means to destroy medical needle 98 successively throughout its length by performing the following operation. When the sharp end of a medical needle 98 is inserted into the apparatus medical needle aperture 30 and through medical needle sensor 96. Stationed directly above the upper electrode assembly 106 and directly below the medical needle aperture 30 is contained a metal piece resembling coil of wire with a known electrical inductance. The metal piece, having an equivalent calculated number of turns of wire, is shaped into a geometry such that the medical needle passes through the lines of magnetic flux generated by the inductor. The presence of the needle inserted through the through the upper contact assembly is determined by monitoring the change in inductance of the sensor coil.

The output of the sensor is monitored by computer 66 and the computer checks the state of the battery for the proper charge required to dispose of the needle by monitoring the status of the battery charger 64. If no capacity to incinerate the medical needle 98 is available as is known a priori, the present invention 10 will not operate and display that information on the front panel status indicators 14. If the rechargable battery 54 is properly charged, the fan 86 will be activated to establish the flow in and around the burn unit assembly 90. The module power switch 62 is activated when the rechargable battery 54 is fully charged and the medical needle 98 is sensed by computer 66 through the medical needle sensor 96. The module power switch 62 connects the rechargable battery 54 to the burn module 16 when there is sufficient energy to destroy the medical needle.

With air flow established by fan 86, the medical needle 98 is continuously inserted through burn unit assembly housing 104, and contacts the upper electrode assembly 106. The upper electrode contactor 112 is displaced to accommodate needle with constant compression generated by retainer spring 110 against said needle. The needle continues through upper insulator 114, enters the moveable electrode 116, continues through lower insulator 118, and completes an electrical circuit between upper electrode assembly 106 and lower electrode 120. The computer senses the completed electrical circuit and engages the left motor drive assembly 124. Thereafter, a plurality of simultaneous operations occur. The moveable electrode upper wiper 138 contacts said needle and invokes an electrical short-circuit through a portion of the needle equal to the distance between the said electrodes, the moveable electrode waste cover 140 creates an opening to the waste cavity 142, and moveable electrode lower wiper 136 directs the debris into the waste cavity 142.

The moveable electrode 116 has the same electrical potential as the lower electrode 120 and is secured to left motor drive assembly 124 on one end and the right motor drive assembly 126 on the distal end. The left motor drive assembly 124 and right motor drive assembly 126 are used to supply a force or moment to the movable electrode retainers 132 to move the moveable electrode 116 across the path of the upper electrode assembly 106 and the lower electrode 120 and perpendicular to the medical needle 98 insertion path in a push-pull manner. The initial position of the moveable moveable electrode 116 is immediately outside the perimeter of the upper electrode assembly 106 cutout opening, lower electrode 120, and space between said electrodes. Other devices can also be used to supply torque whereby the moveable electrode 116 will cross the path of upper electrode assembly 106, cutout opening, and lower electrode 120. The electrodes (the upper electrode assembly 106, the lower electrode 120, and the moveable electrode 116) are connected the rechargable battery 54 via burn head electrode connectors 130. All electrodes are composed of high electrically conductive materials.

When the circuit is broken, by destroying the successive length of said needle, and the needle burn is completed the third movable electrode (moveable electrode 116 ) returns to its at rest position. The plastic/glass portion of the needle with the blunted and sealed needle nub is then withdrawn from the needle receiving means by the user. It can be retrieved for recycling or can be disposed of by any conventional waste handling methods. The fan 86 continues to run for a sufficient period to fully void the burn module 16 of any toxic gases or pathogens. The present invention is now ready for reuse.

CONCLUSIONS, RAMIFICATIONS, AND SCOPE

Accordingly, it can be seen that the present invention provides a highly reliable, lightweight, portable, and safe device that can be used by persons of almost any age and training and background.

While our above description contains many specificities, these should not be construed as limitations on the scope of the invention, but rather as an exemplification of one preferred embodiment thereof. Many other variations are possible. For example the medical needle sensor 96 comprised of a coil could be replaced by an equivalent optical sensor within the same form factor.

Although the description above contains many specificities, these should not be construed as limiting the scope of the invention but as merely providing illustrations of some of the presently preferred embodiments of this invention. Various other embodiments and ramifications are possible within it's scope. For example, as battery technology improves, it is expected that lighter weight, higher capacity batteries could replace the typical rechargable battery 54.

Thus the scope of the invention should be determined by the appended claims and their legal equivalents, rather than by the examples given.

We claim as our invention, not only the embodiments as illustrated and described herein, but any variation, modification, or equivalent of the embodiments thereof, within the scope of the invention as set forth in the following claims:

We claim:

1. A device for rendering biologically hazardous medical needles, the medical needles having an electrically conductive hollow shaft with one sharp end, incapable of post-use injury by blunting the remaining syringe/needle hub and sealing said syringe/needle hub such that no potential exists for post-use injury either by stick or accidental scratch or infection transmission, comprising:

a main module, a burn module, a signal connector and power connectors to mate the main module and burn module, a module fastener to secure the mating of the main module and burn module, a controller board containing a battery charger, a computer, an input protector for power, a burn module switch, and a signal connector, said main module comprising:

a base portion with a plurality of mounting provisions for the controller board, burn module protection device, rechargable battery, signal connector, power connectors, power switch, power connector, and wiring harness, a upper portion with front, side, end, top, and slope surfaces, a handle, and a plurality of mounting provisions for connecting the base and upper portions, and mounting provisions for status indicators, said burn module comprising a burn module base portion with a plurality of mounting provisions for the burn module signal connector, the burn module power connectors, the burn unit assembly, the fan, the multi-stage filter, air inlet opening, air exit opening, and the left and right motor drive assemblys, a medical needle sensor, and an identification unit, a burn module cover containing the medical needle aperature and the burn module fastener hole.

2. Said burn module assembly according to claim 1, further comprising a medical needle sensor an burn module identification means (ie serial number) and timer to limit unit lifetime, an upper electrode assembly fixed relative to the burn assembly housing a lower electrode fixed relative to the burn assembly housing a moveable electrode between the upper electrode assembly and lower electrode a fan controlled by said computer, a multi-stage filter for any said needle burn generated airborne toxins, bacteria, smells, or other gases required by the FDA for device approval, left and right motor drive assemblies controlled by said controller board in said main housing an integral waste container said moveable electrode is accuated by left and right motor assemblies controlled by said controller board in said main module via said signal connector said moveable electrode provides electrical contact to said medical needle for the cutting, blunting, sealing and to move the waste to said waste container and to prevent the waste from leaving the container.

3. A controllable and moveable electrode for medical needle disposal according to claim 2 comprising a plurality of signals generated by said controller board based on electrical resistance of the medical needle and supplying, upon activation, a selected control signals, a connecting means to transfer the selected signal from the main module and burn module via a signal connector left and right motor assemblies receiving said selected control signals a disabling means for disabling said moveable electrode upon completion of medical needle burn process.

4. The device, according to claim 1, wherein the burn module can be removed in a modular fashion at any time and after exhaustion of capacity to destroy said medical needles by statusing said identification means.

* * * * *